United States Patent
Mirzabekov et al.

(10) Patent No.: US 6,465,174 B1
(45) Date of Patent: Oct. 15, 2002

(54) RAPID METHOD TO DETECT DUPLEX FORMATION IN SEQUENCING BY HYBRIDIZATION METHODS, A METHOD FOR CONSTRUCTING CONTAINMENT STRUCTURES FOR REAGENT INTERACTION

(75) Inventors: Andrei Darievich Mirzabekov, Moscow (RU); Gennadiy Moiseyevich Yershov, Zelenograd (RU); Dmitry Yuryevich Guschin, Hinsale, IL (US); Margaret Anne Gemmell, Western Springs, IL (US); Valentine V. Shick, Moscow (RU); Dmitri Y. Proudnikov, Samara (RU); Edward N. Timofeev, Moscow (RU)

(73) Assignee: University of Chicago, Chicago, IL (US)

( * ) Notice: Subject to any disclaimer, the term of this patent is extended or adjusted under 35 U.S.C. 154(b) by 0 days.

(21) Appl. No.: 09/127,313

(22) Filed: Jul. 31, 1998

Related U.S. Application Data

(60) Continuation-in-part of application No. 09/096,020, filed on Jun. 11, 1998, which is a division of application No. 08/592,120, filed on Jan. 26, 1996, now Pat. No. 5,861,247.

(51) Int. Cl.[7] ............................. C12Q 1/68; C07H 21/00
(52) U.S. Cl. .................................. 435/6; 536/25; 536/4
(58) Field of Search ........................... 427/209; 436/527, 436/528; 435/6, 91.2; 536/25.4

(56) References Cited

PUBLICATIONS

Proudnikov, et al. "Immobilization of DNA in Polyacrylamide Gel for the Manufacture of DNA and DNA_Oligonucleotide Microchips", vol. 259, pp. 34–41. (1998 Analytical Biochemistry).

Guschin, et al. "Manual Manufacturing of Oligonucleotide, DNA, and Protein Microchips". vol. 250, No. 2, pp. 203–211. (1997 Analytical Biochemistry).

Vasiliskov et al. Bio Techniques 27(3): 592–604 (1999).*

* cited by examiner

*Primary Examiner*—Lisa B. Arthur
(74) *Attorney, Agent, or Firm*—Cherskov & Flaynik

(57) ABSTRACT

A method for determining the existence of duplexes of oligonucleotide complementary molecules is provided whereby a plurality of immobilized oligonucleotide molecules, each of a specific length and each having a specific base sequence, is contacted with complementary, single stranded oligonucleotide molecules to form a duplex so as to facilitate intercalation of a fluorescent dye between the base planes of the duplex. The invention also provides for a method for constructing oligonucleotide matrices comprising confining light sensitive fluid to a surface, exposing said light-sensitive fluid to a light pattern so as to cause the fluid exposed to the light to polymerize into discrete units and adhere to the surface; and contacting each of the units with a set of different oligonucleotide molecules so as to allow the molecules to disperse into the units.

20 Claims, 8 Drawing Sheets

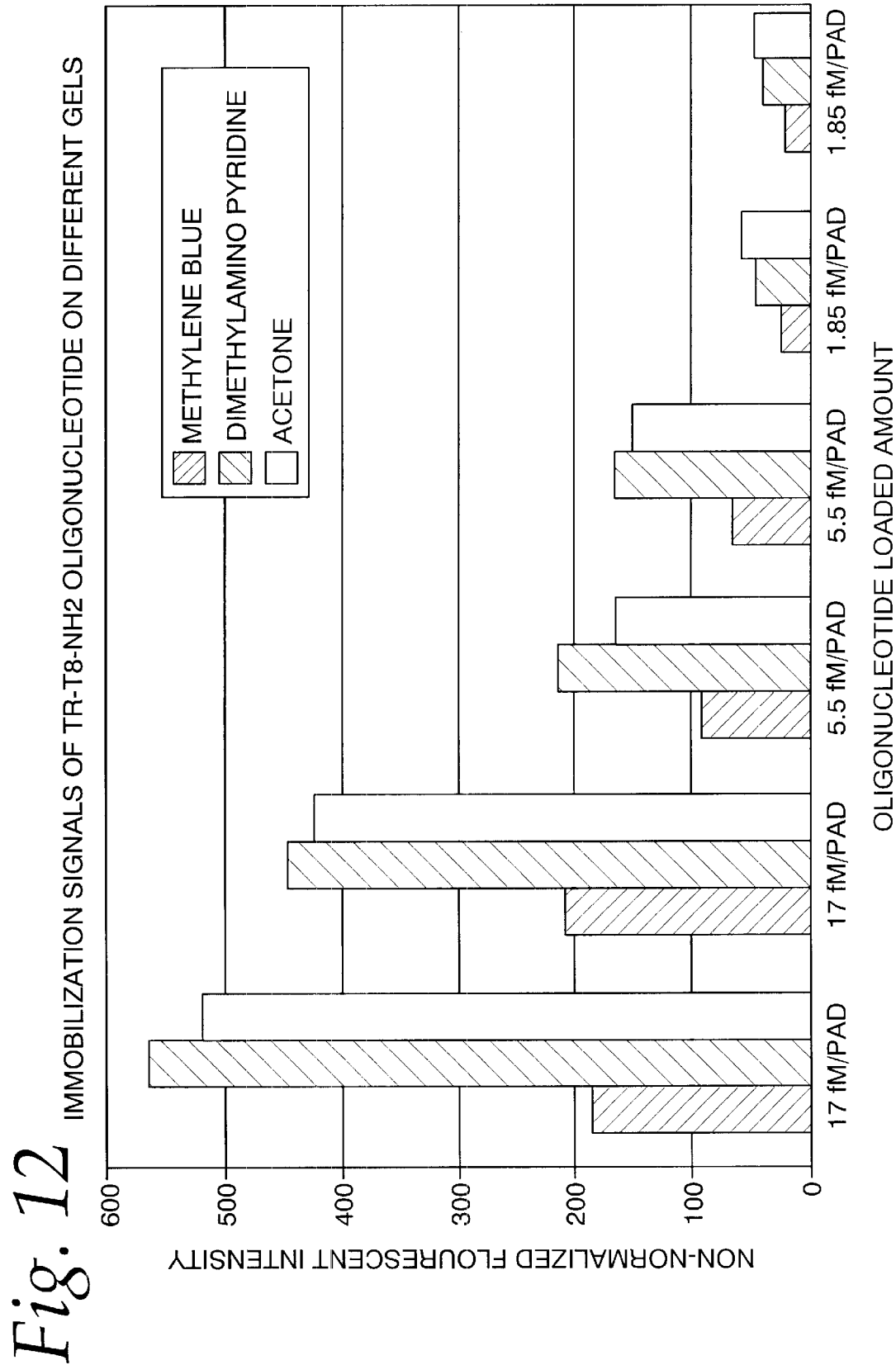

RAPID METHOD TO DETECT DUPLEX FORMATION IN SEQUENCING BY HYBRIDIZATION METHODS, A METHOD FOR CONSTRUCTING CONTAINMENT STRUCTURES FOR REAGENT INTERACTION

This application is a Continuation-In-Part of Ser. No. 09/096,020, filed on Jun. 11, 1998 and still pending which is a divisional of application Ser. No. 08/592,120, filed on Jan. 26, 1996, now U.S. Pat. No. 5,861,247.

STATEMENT REGARDING FEDERALLY SPONSORED RESEARCH OR DEVELOPMENT

The United States Government has rights in this invention pursuant to Contract No. W-31-109-ENG-38 between the U.S. Department of Energy and the University of Chicago representing Argonne National Laboratory.

BACKGROUND OF THE INVENTION

1. Field of the Invention

This invention relates to a method for rapidly detecting the presence of duplex formation between single stranded nucleotide macromolecules, and more specifically, this invention relates to a method for using oligonucleotide arrays to rapidly detect duplex formation of oligonucleotide sequences. This invention also relates to a simple procedure for producing the oligonucleotide-arrays.

2. Background of the Invention

Present techniques for determining the existence of target sequences in patient DNA are complex, inefficient and somewhat time consuming. For example, one multistep DNA sequencing approach, the Maxam and Gilbert method, involves first labeling DNA, and then splitting the DNA with a chemical, designed to alter a specific base, to produce a set of labeled fragments. The process is repeated by cleaving additional DNA with other chemicals specific for altering different bases, to produce additional sets of labeled fragments. The multiple fragment sets then must be run side-by-side in electrophoresis gels to determine base sequences.

Another sequencing method, the dideoxy procedure, based on Sanger, et al. *Proc. Natl. Acad. Sci. USA* 74, 5463–7 (1977) first requires the combination of a chain terminator as a limiting reagent, and then the use of polymerase to generate various length molecules, said molecules later to be compared on a gel. The accompanying lengthy electrophoresis procedures further detracts from the utility of this method as a fast and efficient sequencing tool.

A more recently developed sequencing strategy involves sequencing by hybridization on oligonucleotide microchips, or matrices, (SHOM) whereby DNA is hybridized with a complete set of oligonucleotides, which are first immobilized at fixed positions on a glass plate or polyacrylamide gel matrix. There are drawbacks to this technique, however. For instance, given that short nucleotide sequences are repeated rather frequently in long DNA molecules, the sequencing of lengthy genome strings is not feasible via SHOM. Also, hybridization with short oligonucleotides is affected by hairpin structures in DNA.

Furthermore, SHOM requires the utilization of high volume substrates containing many thousands of cells. If immobilized octamers are utilized to determine the positions of each of the four bases in genomic DNA, for example, then $4^8$ or 65,536 such octamers, themselves which would need to be previously fabricated, would have to be immobilized in individual cells on the gel matrix.

The production of literally thousands of these cells on the polyacrylamide substrates is problematic. First, these cells must be accurately spaced relative to one another. Second, these cells must be of sufficient depth and volume to hold predetermined amounts of the oligonucleotide. Cell sizes can range from 25 microns ($\mu$m) to 1000 $\mu$m.

Typically, cells are produced in a myriad of ways. Two-dimensional scribing techniques and laser evaporation are two typical methods of cell formation. Mechanical scribing techniques are limited, however, in that the smallest structures which can be produced via this method are approximately 100 $\mu$m×100 $\mu$m. Lasers applications, because of their expense, also are limiting. Furthermore, both of these procedures require complex equipment and experienced personnel.

A need exists in the art to provide a rapid and efficient method for detecting the existence of complementary sequences to target DNA strands. This detection method should be performed using standard reagents found in a typical biochemistry facility. A need also exists for a method to produce accurate polyacrylamide matrices to be used in the above-disclosed duplex detection method. Such a matrix production method also must be simple enough to be performed in typically-equipped biochemical laboratories.

SUMMARY OF THE INVENTION

It is an object of the present invention to provide a method for rapidly detecting the formation and existence of duplexes between complementary nucleotide sequence strands that overcomes many of the disadvantages and reliability shortcomings of the prior art.

Another object of the present invention is to provide a method for the detection of DNA duplexes. A feature of the invention is the use of intercalating dyes. An advantage of the invention is the rapid detection of duplexes using typically-outfitted laboratories to perform standard procedures with common reagents.

Yet another object of the present invention is to provide a highly efficient method for detecting DNA duplexes. A feature of the invention is contacting a DNA duplex, contained on a high-volume support substrate, with an intercalating agent. An advantage of the invention is the enhanced ability to detect small amounts of formed DNA duplexes using standard, low-cost laboratory reagents.

Still another object of the invention is to provide a method for producing a polyacrylamide matrix having thousands of individual and well defined holding cells. A feature of the invention is the use of mask-controlled photopolymerization processes. An advantage of the invention is the rendering of high numbers of precise cell geometries and at high densities.

Another object of the present invention is to provide an enhanced method for making arrays to contain oligonucleotide molecules. A feature of the invention is the use of a photosensitive mask with a means for confining reaction fluid, which comprises the array elements, to a light-exposed region during fluid photopolymerization. An advantage of the invention is that the confining means serves to maintain fluid concentration across the array pattern, thereby assuring equal curing and therefore consistency of all of the array elements.

Yet another object of the present invention is to provide a highly sensitive oligonucleotide display array. A feature of the invention is enabling a photopolymerization process of array elements using colorless radical photoinitiators. The photoinitiators have strong absorption maxima at between 180 to 280 nanometers (nm) and are able to produce radicals upon UV radiation. The fluorescence of these photoinitiators are negligible at 400 to 800 nm. An advantage of the invention is the decrease in background fluorescence from gel element constituents and therefore an increase in sensitivity during duplex detection analysis.

Still another object of the present invention is to provide a method for standardizing sequencing and hybridization processes on micro matrices. A feature of the invention is the use of strictly-controlled oligo transfer means. Another feature is comparing the fluorescence intensity of labeled oligomer placed at predetermined positions on the micro matrices to other regions of the micro matrices contacted with labeled, mobile oligomers. An advantage of the invention is the ability to reproduce the hybridization patterns and to determine the efficiency of the hybridizations.

Briefly, the invention provides for a method for determining the existence of duplexes of oligonucleotide complementary molecules comprising constructing a plurality of different oligonucleotide molecules each of a specific length and each having a specific base sequence; supplying a matrix having a plurality of cells adapted to receive and immobilize the oligonucleotide molecules; immobilizing the different oligonucleotide molecules in the cells to fill the cells; contacting the now-filled cells with single stranded oligonucleotide molecules to form a duplex; contacting the duplex with an intercalating agent; and observing fluorescence levels emanating from the now-contacted duplex.

The invention also provides for a method for constructing oligonucleotide matrices comprising confining light sensitive fluid to a surface, exposing said light-sensitive fluid to a light pattern so as to cause the fluid exposed to the light to coalesce into discrete units and stick to the surface; and contacting each of the units with a set of different oligonucleotide molecules so as to allow the molecules to disperse into the units.

The invention further provides for a method for constructing oligonucleotide matrices comprising confining light-sensitive monomer solution to a surface, expo-sing said light-sensitive monomer to a predetermined light pattern so as to cause monomer in solution exposed to the light to polymerize into uniform, discrete gel pads and stick to the surface; and contacting each of the units with a set of different oligonucleotide molecules so as to allow the molecules to disperse into the units

BRIEF DESCRIPTION OF THE DRAWING

The invention together with the above and other objects and advantages will be best understood from the following detailed description of the preferred embodiment of the invention shown in the accompanying drawing, wherein:

FIG. 12 is a graph comparing fluorescence of various photoinitiators, in accordance with features of the present invention.

DETAILED DESCRIPTION OF THE INVENTION

This invention involves incorporating intercalating techniques with processes for sequencing genetic material by hybridization methods (SBH) so as to produce a simple low resolution procedure for duplex formation analysis. This invention also teaches a method to produce polyacrylamide matrices having thousands of microscopic-sized, precisely configured and positioned holding cells designed to contain predetermined quantities of oligonucleotide mixtures.

The inventors have developed a method of using a mask-controlled photo-polymerization process to create micro-matrix topologies. The resulting micro-matrices are used to immobilize specific oligonucleotide strands designed to form duplexes with target DNA. The duplexes are contacted with an intercalating substance or dye to alert clinicians to the presence of duplexes.

Array Manufacturing Detail

The array manufacturing method, noted supra, incorporates a modified Methylene Blue-, or Nonmethylene Blue-induced photo-polymerization procedure whereby a polyacrylamide solution is prepared and then configured into desired shapes and sizes for subsequent polymerization.

Figure 1:
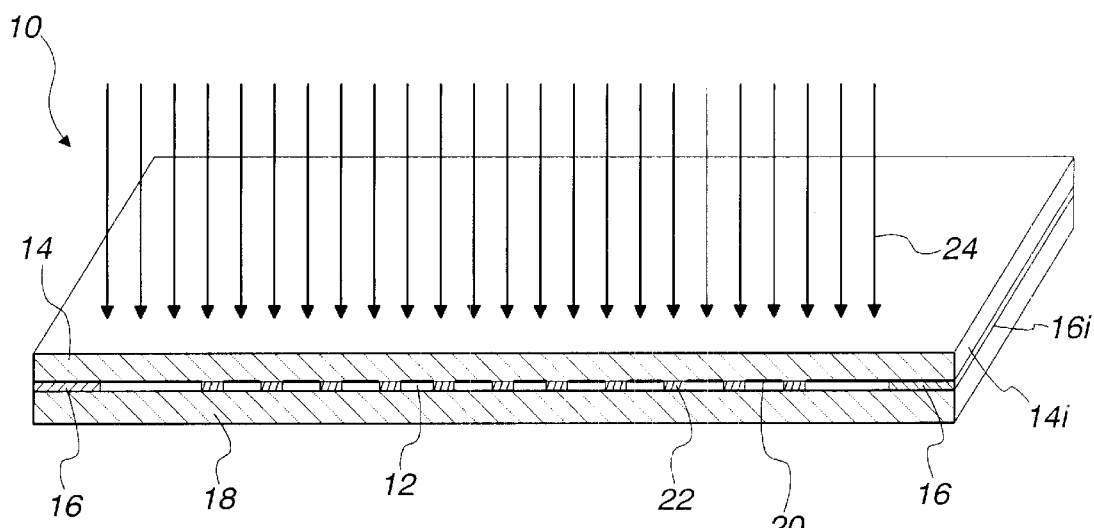
FIG. 1 is an elevated view of an polyacrylamide matrix assembly, in accordance with the present invention.
Figure 2:
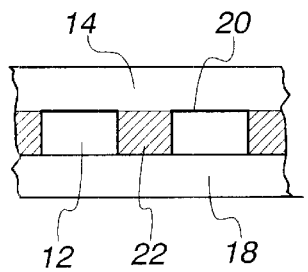
FIG. 2 is a magnified view of the polyacrylamide matrix assembly illustrated in FIG. 1, in accordance with the present invention.

The production of gel-matrices involves the construction of polymerization units into which prepared acrylamide fluids are placed. One exemplary polymerization unit is depicted in FIG. 1, as numeral 10, and partially magnified in FIG. 2.

A liquid (prepolymerized) mixture 12 is applied to a first surface of a quartz substrate 14, which is previously manipulated to contain a photomask. The preparation of the quartz substrate 14 involves applying a mask 20 to the first surface of the substrate 14, and then pretreating the first surface with an anti-wetting agent or an agent to increase the hydrophobicity of the surface. One such anti-wetting agent is a 2 percent solution of dimethyldichlorosilane in 1,1,1,-trichloroethane, having the trade name Repel-Silan™, and manufactured by Pharmacia Biotech of Uppsala, Sweden. Another suitable anti-wetting agent is trimethylchlorsilane. Two identical spacers 16, made from an inert material such as Teflon, of 20 $\mu$m thickness are placed on peripheral edges of the first surface of the quartz substrate so as form a pan-like container to confine the mixture 12. As such, a myriad of spacer thicknesses can be employed, depending on the final desired thickness of the polynucleotide chip.

A glass microscope slide 18, first pretreated with a material to attach polyacrylamide to glass, is placed on top of the spacers 16 to form a glass chamber 10. An exemplary pretreatment material is γ-Methacryloxy-propyl-trimethoxysilane, manufactured as Bind Silane by Pharmacia. This entire assembly or chamber 10 is fastened together via a myriad of fastening means (not shown), such as paper clips, tape, or inert adhesive.

A first surface of the quartz substrate 14 has a nontransparent mask (e.g., comprised of an inert opaque material such as chrome coating or permanent ink), containing a (grid) 20 defining a pattern of the desired topology. The grid 20 is applied to the mask coating surface of the quartz substrate 14 either by hand with a fine point marker or by photolithography, with the size of the gel elements defined by the dimensions of the transparent squares etched into the mask.

Figure 3:
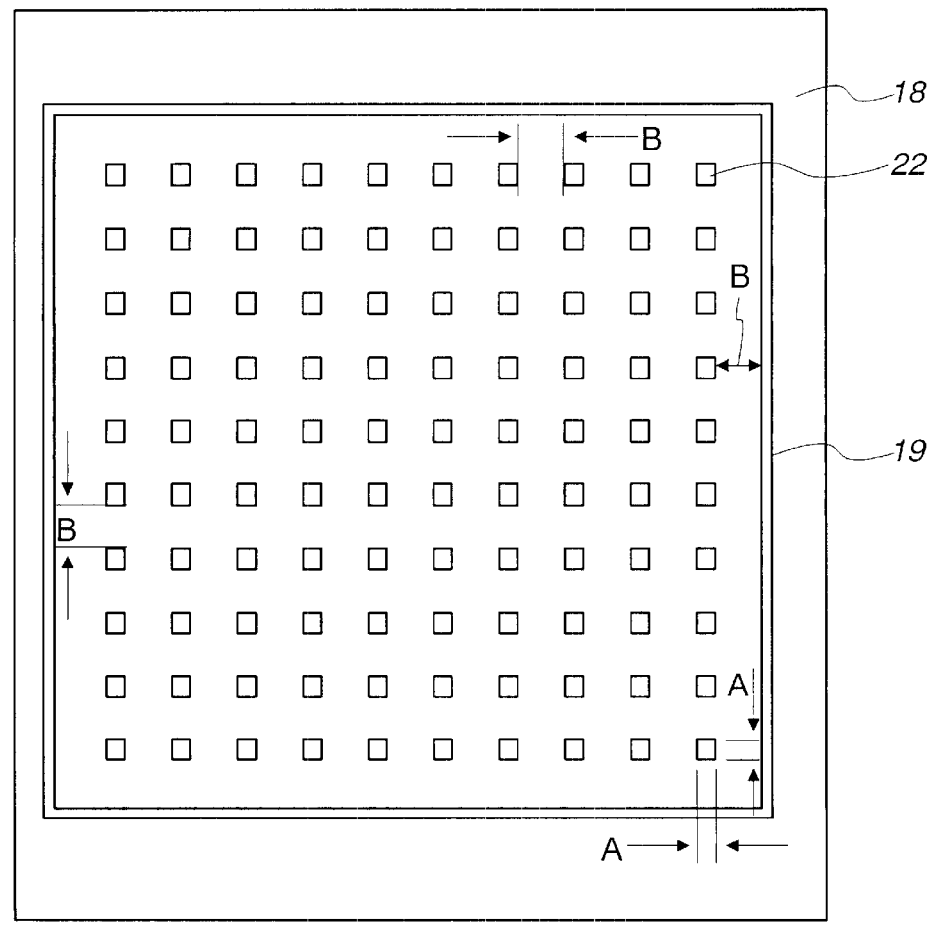
FIG. 3 is a plan view of a gel matrix, manufactured in accordance with the present invention.

An exemplary grid is depicted in FIG. 3. Dimensions labeled as element "A" are the sizes of gel cells while elements "B" are illustrated as the spaces between the cells. The mask is designed to block the light, used in the light-induced acrylamide polymerization process, in the spaces "B" between the gel units 22 where gel coalescence is not desired.

Various sizes of gel cells were fabricated on separate masks, as disclosed in Table 1, below.

TABLE 1

Various Gel and Space Dimensions Obtained Via the Invented Process of Light-Induced Polyacrylamide Polymerization.

| | Dimensions ($\mu$m) | |
| --- | --- | --- |
| Mask # | Gel Cells | Interstitial Spaces |
| 1 | 25 | 50 |
| 2 | 40 | 80 |
| 3 | 100 | 200 |
| 4 | 500 | 1,000 |
| 5 | 1,000 | 2,000 |

After assembly, the assembled polymerization unit 10 is placed under a light source, such as a 312 nm UV-transilluminator such that the quartz substrate is closest to the source. Good results are obtained when the actual photomask layer 20, first deposited on the first surface of the quartz substrate 14, is in contact with the acrylamide solution. UV exposures of approximately 20 minutes provide good results. A myriad of wavelengths are suitable for the light-induced polymerization process, including those found in the range of between approximately 250 nm and 320 nm.

The inventors have found during the photopolymerization process that certain gel elements may cure or polymerize to solid entities before others or that there may be inconsistencies between gel elements in terms of shape, adsorptive characteristics, and volumetric capacities. For example, gel elements located toward the middle of the array seem to have better consistency then those elements arranged along the periphery of the array. The variances in gel consistencies probably is due to concentration variances in the acrylamide solution, whereby solution is polymerized or "taken up" more evenly in a gel unit when that unit is surrounded by other gel units being photo-treated and therefore utilizing solution at equal rates. Inasmuch as gel units along the periphery of the array are not completely surround by flanking or neighboring units, solution concentrations vary, resulting in the appearance and volume of these periphery varying with units toward the middle of the array. This results in a decrease in quality control of the entire array. The quality of periphery units are also more prone to decrease if some of the acrylamide solution leaks through the spacer 16/glass slide 18 interface defining the periphery, and therefore out of the reaction zone.

Surprisingly and unexpectedly, the inventors have found that the provision of an ancillary gel structure resembling a frame, dam or border 19 around substantially the entire array structure, serves to maintain the quality of gel elements across the entire array by eliminating or greatly minimize concentration variances in the acrylamide solution. Optionally, a plurality of dams or borders can be provided, thereby creating an interstitial or buffer area between the two dams or borders. Such a frame or border is also depicted in Gushin, et al. *Analytical Biochemistry*, 250, 2, pp 203–211, the entire teaching of which is incorporated herein by reference.

As with the individual gel elements, the border is comprised of hardened (i.e., polymerized) polyacrylamide solution and is formed between the quartz substrate 14 and glass slide 18 when light 24 passes through a transparent portion of the mask 20 defining the border. Optionally, for even more consistent quality control, the dam or border is arranged to be a same distance B from the periphery gel elements, that other gel elements in the array are spaced from each other.

As noted supra, the border or dam may also prevent leakage of the photo-sensitive solution out of the reaction zone. The border hardens into a solid wall having a first edge and a second edge. The first edge is contacted by an inner surface 14i of the quartz substrate 14 facing the acrylamide solution. The second edge is contacted by an inner surface 18i of the glass substrate 18 contacting the acrylamide solution. Essentially, the first and second edges of the border communicate with the inner surfaces of the quartz substrate and glass substrate so as to prevent seepage of acrylamide solution out of the reaction zone prior to and/or during polymerization.

After exposure, the chamber 10 is disassembled. To facilitate disassembly, the chamber 10 can placed in a water bath at room temperature. As noted supra, gel matrix units 22 are retained on the glass where light is allowed to permeate through the mask. These units 22 are separated from each other as a result of opaque mask portions, between the unit regions, precluding gel polymerization.

The resulting gel matrix is washed with water, placed in a solution for a period of time to introduce functional groups (e.g., hydrazide groups) into the acrylamide (an exemplary solution being hydrazine hydrate). This period of time can range from 35–45 minutes. The matrix is then washed with water, and then treated to neutralize the remnants of the basic pH hydrazine treatment. One such neutralization procedure is placing the matrix in 1 percent acetic acid until neutralization is achieved, perhaps for 10 minutes. After neutralization, the matrix is washed with water, and then treated to remove any electrostatically sorbed chemicals. One such treatment involves placing the matrix in 1 M NaCl for approximately 10 minutes. After a final washing with water, the unit is left to dry, and then treated with a thin film of an anti-wetting agent, such as Repel-Silan so as to make the interstitial glass spaces, designated as "B" in FIG. 3, hydrophobic. This will further isolate the gel units 22 from each other to minimize cross contamination during oligonucleotide loading. Treatment of the anti-wetting agent is brief, approximately 1 minute. The matrix is rendered ready for oligonucleotide loading after a final washing with ethanol (from 96 percent to neat) and then water to remove the ethanol.

Acrylamide Liquid

Preparation Detail

A salient feature of the acrylamide solution is the incorporation of photo initiating agents to activate the polymerization via free radical reactions. Agents which are radical producing upon a selected stimuli (such as UV light) are suitable. For example, in one exemplary photopolymerization process, light is directed on a solution containing 40 percent (between 30–45 percent, is suitable) acrylamide/Methylene Bis-Acrylamide (30:1) stock solution and 0.04 percent Methylene blue stock solution in water. The stock acrylamide solution is diluted with water to a concentration ranging from 4 to 8 percent and subsequently degassed with a water pump for 10 minutes. The gel matrix is prepared from a standard mixture of 0.5 $\mu$l 0.04 percent Methylene blue solution, 1 ml acrylamide solution and 10 $\mu$l N,N,N', N'-tetramethylethilendiamine (TEMED), from Aldrich (Milwaukee, Wis.).

While the acrylamide solution containing methylene blue provides suitable polymerization mixtures, the inventors have recently developed polymerization mixtures containing radical photoinitiators having no fluorescence. Surprisingly and unexpectedly, these recent developments has resulted in enhancing the sensitivity of subsequent hybridization determinations inasmuch as the new solutions do not fluoresce at the range of 400–800 nm. As such, background noise due to unwanted fluorescence is eliminated or minimized.

The following compounds successfully initiate polymerization of acrylamide solutions with UV light but without the background fluorescence associated with methylene blue. These agents produce radicals under UV irradiation that facilitate the polymerization process:

1. 2,2-dimethoxy-2-phenyl acetophenone;
2. dimethylamino-pyridine;
3. 3,5-diiodo-4-pyridone-1-acetic acid;
4. 4,4'-azobis(4-cyanovaleric acid);
5. 4(dimethylamino)phenethyl alcohol; and
6. acetone.

Choices 1–5 above are available through Aldrich Chemical Co., Milwaukee, Wis., with choice 6 available through any chemical supply outlet, including Fisher Scientific of Pittsburgh, Pa.

The stock solution for the polyacrylamide gel micro matrix also contains the following constituents:

A. 5 percent acrylamide/bis solution in a 19/1 molar ratio (available through BIORAD Laboratories, Hercules, Calif.;
B. 40 percent glycerol (Fisher Scientific);
C. 0.05 percent monomer capable of generating aldehydes when irradiated, one such monomer as N-(5,6-di-O-isopropylene)hexylacrylamide as described in Timofeev et al, *Nucl. A. Res.* 1996, 24, 16 and incorporated herein by reference. The monomer is necessary so as to facilitate immobilization of amino compounds such as oligonucleotides, DNA, proteins and moieties having primary amino groups.
D. 50 percent sodium phosphate buffer (0.2 M, pH 7.0) (Fisher);
E. 1.2 percent TEMED (Not required for initiator choices 1 and 6.) (Available through BIORAD.); and
F. Initiator # as enumerated above:
   1. 0.125 percent or higher;
   2–5. 0.04 percent or higher; and
   6. 0.8 percent or higher.

Surprisingly and unexpectedly, the inventors have determined that acrylamide and bisacrylamide by themselves are capable of polymerizing in the presence of UV without the presence of other radical producing agents. In these instances, an exemplary suitable reaction mixture is comprised as follows:

1 ml 40 percent acrylamide (19/1 acrylamide/bis) 3.2 ml glycerol;

3.48 ml buffer (0.2 M phosphate buffer);

0.32 ml of 12.5 mg/ml of 5,6-di-O-isoproplylidene hexyl acrylamide.

The above exemplary solution is degassed for 10 minutes and then subjected to UV radiation for approximately 30 minutes.

Gels obtained using nonmethylene blue-containing prepolymerized liquids exhibited low background fluorescence in the range of between 490 and 650 nanometers. For example, at the wavelength of Texas Red fluorescence excitation, the gels showed emission of about 1 percent of the glass support level or less. As such, the resulting gels are considered non-fluorescent.

At the wavelength typical of fluorescein emission, gels manufactured by non-methylene blue electron acceptors showed the highest background fluorescence. However this fluorescence was one-tenth that obtained with methylene-blue containing polymerization liquids.

At 580 nm and longer wavelengths, the fluorescence of acetone polymerized gels drops a 1000 fold compared to the fluorescence levels obtained with methylene blue is used. Polymerization was tested at pH 5.0 (Na-acetate buffer), at pH 8.5 (Na-borate buffer), neutral pH (Na-phosphate buffer), and TAE-buffer (which is a buffer used in agarose gel electrophoresis).

Relative fluorescent intensity (after factoring out background intensity) of methylene blue and two of the non-dye activators is depicted in FIG. 12. As can be seen with gel pads loaded with 17 femtomoles of loaded oligonucleotide, non-dye activators exhibited a three-fold increase in fluorescence intensity compared to methylene-blue containing photopolymerization liquors. Pads loaded with 5.5 fM/pad and 1.85 fM/pad experienced at least a two-fold increase in fluorescence activity.

Polymerization proceeds at myriad wavelengths, particularly at wavelengths between 254 nm and 312 nm, and generally is completed in between 15–30 minutes. At shorter wavelengths polymerization proceeds at a faster rate. However, polymerizations at longer wavelengths (i.e., in the visible spectrum) may be preferable due to enhanced simplicity and safety considerations.

The polymerization process is oxygen-sensitive. As such, for optimal results, a deaeration procedure should be applied under controlled pressure (i.e., utilizing a vacuum pump) and for a sufficient time, determined experimentally. Usually, an exposure time of between 2 to 5 minutes is suitable.

Oligonucleotide

Loading Detail

The inventors have developed a specific method for loading oligonucleotides onto matrices which are produced via the method outlined above. The method is fully disclosed in PCT/RU94/00179, filed on Aug. 11, 1993 to Mirzabekov and incorporated below. Described briefly, a pin is immersed into, and is wetted with, oligonucleotide solution. After being withdrawn from the solution, the pin is contacted with the gel surface.

During oligonucleotide aspiration, transfer and deposition, the temperature of the pin must be maintained near dew point at ambient temperature so as to prevent evaporation. Otherwise, the viscosity of the solution micro-volumes (typically 10 nanoliters or less) will lead either to complete evaporation or to incomplete transfer of the desired dose.

The invented transfer method allows for the transfer of a range of micro-volumes of oligonucleotide solutions, from 0.3 to 50 nanoliters (nl), with a dispensing error of no more than approximately ±20 percent.

As disclosed in the above-identified PCT application PCT/RU94/00179, the device for micro dispensing aqueous solutions of solutions is depicted in FIGS. 6–10. The device comprises a base 1 shaped as a rectangular plate, one side of which carries a plurality of rods 2 held with one of their ends to said plate. The rods 2 are arranged parallel to one another and spaced equidistantly to one another. Butt ends 3 of the rods are coplanar with one another and parallel to the base 1. A battery 4 of thermoelectric cells (e.g. Peltier elements) adjoins the base 1 on the side opposite to that equipped with the rods 2 and is in heat contact therewith. In this particular embodiment, the battery 4 is shaped similar in size to the base 1. The battery 4 is connected through wires, 5, to a controlled source 6 of direct-current. The battery 4 of thermoelectric cells is a means for maintaining the temperature of the butt ends 3 of the rods 2 equal essentially to the dew point of the ambient air. With its other side, the battery 4 of Peltier elements adjoins the surface of a flow-block radiator 7 and is in heat contact therewith. To provide a uniform heat contact between the surface of the battery and the base on one side, and between the radiator 7 on the other side, provision is made for thin (under 100 microns thick) layers 8 of a heat-conductive paste based on beryllium oxide and polydimethyl-siloxane oil.

The base 1 and the rods 2 are made from a material having high thermal conductivity, preferably from a metal, such as copper or brass. The radiator 7 can be a silicon slab.

The rods 2 are provided with a heat-insulating coating 9 applied to half their length, including from the point of the rod attachment to the base plate 1. Material for the coating in this region can be polyolefin. One polyolefin product is Heat Shrinkable Pack, available through RS Components Ltd., England. The heat insulating coating 9 used to protect the surface of the base 1 exposed to atmospheric air can be formed polyurethane.

The rods 2 in the embodiment illustrated are round in cross-section (though they may have any other cross-sectional shape) and their vacant ends are shaped as cone frustums tapering to the ends. A hydrophilic coating 30 such as glass or gold, is applied to the butt ends 3 of the rods 2, whereas a hydrophobic coating 11 such as fluoroplastic, or glass whose surface is hydrophobized by treatment with Repel Silane, is applied to the side surfaces of the vacant ends of the rods.

The area of the butt ends 3 of the rods is selected such as to obtain the required volume V of the dose being transferred and to obey the following relationship: $V \approx 1/3 \pi R^3 \cdot 10^{-6}$ nanoliters, where V is the required volume of the droplet forming on the butt rod end after the rod has been withdrawn from the solution, and R in microns is the radius of the butt rod end.

The device as described above is used as follows to facilitate liquid transfer: The base 1 carrying the rods 2 are positioned opposite to the tray 32 in such a manner that each rod is located against a respective well 13 of the tray 32 filled with an aqueous solution 34 of the substance to be transferred, e.g., an aqueous oligonucleotide solution. Then the base 1 is displaced towards the tray 12 until the ends of the rods 2 (FIG. 9b) contact the solution 34. Then, by displacing the base 1 together with the rods 2, (FIG. 9c) in the opposite direction, the rods 2 are withdrawn from the solutions, with the result that a microdose 15 (FIG. 9d) of the solution of the substance is formed on the butt end of each rod 2. The volume V of the microdose is independent of the depth of immersion of the rod 2 into the solution 34 (due to the hydrophilic butt end of the rod and hydrophobic coating on the rod's side surface with respect to the solution being transferred) and is determined substantially by the radius R alone of the butt end of the rod 2.

Next, the base, together with the rods loaded with the microdoses of the solution, is transferred to the gel elements 22 arranged in a micro matrix of the type depicted in FIG. 3. The layout of the gel elements 22 complement the configuration of the oligonucleotide-loaded rods so that when the base 1 is positioned opposite to the surface of the matrix, each rod 2 is opposing a respective gel element 22. Thereupon, the base 1 is displaced towards the matrix 18 along the arrow as depicted in FIG. 10b, until the microdoses 15 contact the gel areas 22. During transfer, the temperature of the solution 34 and the butt ends 3 are maintained at the dew point of the air to minimize evaporation of the solution during the transfer. Control of the temperature of the butt ends 3 are attained by changing the battery 4 voltage of the thermoelectric cells in response to the signal produced by a temperature transmitter (not shown) in heat contact with the base.

Upon contact with the microdose 15, the gel element 22 vigorously absorbs the solution (FIG. 10c), with the result that the gel areas 22 swell and the microdoses are drawn into the gel.

After fluid transfer, the base 1 supporting the rods 2 is retracted from the micro matrix. The rods then are washed and dried for reuse.

The inventors have found that the micro-volumes of the transferred oligonucleotide can be reproducibly controlled via the transfer pin 2, discussed supra, that is thermostabilized. The pin can be solid metal, or a glass fiberoptic pin which is plated with a hydrophobic thermal conductor. A myriad of thermal conductors are suitable, including but not limited to gold, copper, brass, silver, or various alloys. An exemplary manual pin device is the gold-plated, glass fiberoptic pin available from Faberguide Industries of Stirling, N.J. The pin has a 240 µm diameter for its hydrophilic tip 3 and a hydrophobic side surface. A more thorough disclosure of the use of gold-tipped transfer means in contained in the Gushin et al. reference cited earlier, and incorporated herein by reference.

Such a metal-clad pin offers advantages over pins comprised of bad thermal conductors (such as Teflon) inasmuch as the metal serves to evenly distribute the temperature (regulated by the Peltier element 4) over the entire pin to maintain the oligo-droplet at or near dew point. Surprisingly and unexpectedly, the inventors also found that gold-clad pins have high durability inasmuch as the cladding does not detach or pull away from the underlying substrate to form a capillary cavity, even after several thermal cyclings. This is crucial inasmuch as the formation of such a cavity otherwise causes wicking which distorts the droplet formed on the tip 3 and decreases volume of the droplet. This leads to droplet-volume variances and therefore quality control problems.

Oligonucleotide Immobilization Detail

The inventors have developed an immobilization procedure for coupling micromolecules to acrylamide gels so as to minimize liquid evaporation during immobilization and to also ensure that covalent bonding of oligonucleotides to the gel matrix units proceeds to completion. This procedure is more fully disclosed in PCT/RU94/00178, filed on Aug. 11, 1993, to Yershov, and incorporated below.

Briefly, the immobilization process is as follows: Microvolumes of bioorganic solutions are loaded onto the micromatrix cells, with the temperature of the micro-matrix being maintained equal to that of the ambient air. Once the micro-volumes of the oligonucleotide solutions have been applied to the cells of the matrix, the micro-matrix temperature is set equal to or below the dew point of the ambient air. This temperature is maintained until swelling of the gel is complete and noncoalescent droplets of water condensate appear in the spacings "B" between the cells.

After the appearance of the water condensate, a thin layer of an inert, nonluminescent oil is applied to the micro-matrix surface so as to prevent oligonucleotide evaporation. An oil layer of at least approximately 100 μm provides good results. A myriad of inert oils are suitable including, but not limited to, purified Vaseline®, phenyl (10 percent) methylsilicone oil, phenyl (20 percent) methylsilicone oil, among others.

The micro-matrix is kept under the oil layer until completion of the oligonucleotide immobilization process, and preferably for 48 hours. The oil is then removed by washing with a polar substance that will not cause oligo denaturing, such as ethanol, or water. The matrix is dried and stored indefinitely, ready for use.

During application of oligonucleotides, the gel pads are dried immediately to confine the applied oligonucleotides within their respective pad. However, the immobilization of the oligonucleotide (i.e., DNA) with the aldehyde groups found in chemical moieties which comprise the gel is a two step process that is carried out in water. The process involves first the formation of an aldimine bond between the gel's aldehyde groups and the oligo's amino group and, second, reduction of the aldimine group.

A water environment is required in order for the above two-step process to occur. However, water also facilitates cross-talk or contamination of one oligo-loaded gel by a near-by loaded gel. To avoid such contamination, and oligo-transfer inhibitor is used, such as chloroform or other solvent. In an exemplary procedure, a glass plate containing dried gel pads and loaded with oligo is placed under chloroform containing a reducing agent. One such reducing agent is 100 mM pyridinium borane in chloroform. This chloroform layer is then covered with water. Water partly diffuses into the chloroform and migrates through the chloroform layer to the gel pads. The gel pads, upon contacting the water, begin to swell, thereby allowing the reducing agent contained in the chloroform layer access to the constituents in the pads. As such, this procedure allows reducing agent to contact the gel pads to facilitate oligo immobilization while also preventing oligo cross-talk between adjacent, differently loaded gel units.

After the two step immobilization procedure, gel pads are washed with acetone, water and then dried, according the protocol described in Proudnikov et al. *Analytical Chem.* Vol 259, pp34–41, 1998, and incorporated herein by reference. That reference describes immobilization procedures on matrices which contain aldehyde producing agents such as N-(5,6-di-O-isopropylidene)hexylacrylamide.

As disclosed in the above identified PCT application PCT/RU94/00178, the process is illustrated in FIG. 11, wherein a fragment of the micro matrix 18 is shown in a sectional side-elevational view. FIG. 11a depicts the immobilization sequence at the instant when micro volumes of bioorganic solutions 15 are being loaded to the gel elements 22. At this point, the temperature of the micro matrix 18 is maintained equal to that of the ambient air.

Figure 11A:
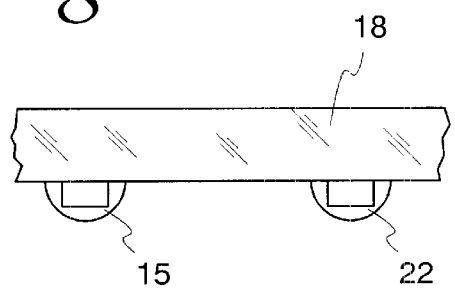
FIGS. 11A–D is a detailed elevational view of a loaded gel element in progressive stages of development, in accordance with features of the invention.
Figure 11B:
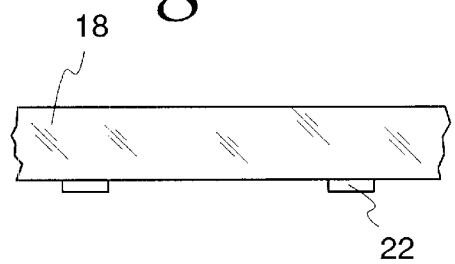

As is depicted in FIG. 11b, at the completion of loading, all residual droplets of the bioorganic solution 15 evaporate, and the condition of the gel is the same in all cells.

Figure 11C:
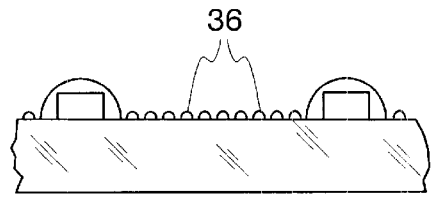

At the instant when the water condensation from the ambient air has been completed, the temperature of the micro matrix 18 is below or equal to the dew point of the ambient air. The gel cells 22 have swollen and are coated with water condensate 36. Minute droplets of condensate also appear in the intercell spacings. As depicted in FIG. 11c, the droplets do not coalesce with one another.

Figure 11D:
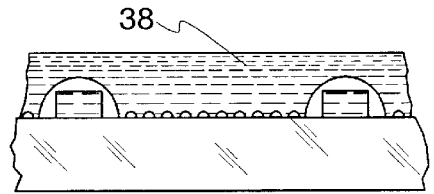

FIG. 11d depicts the entire assembly coated with the film 38 of the nonluminescent oil, with a thickness of over 100 microns. The temperature of the micro matrix is equal to that of the ambient air.

This aforementioned process is applicable for immobilizing any water-soluble bioorganic substances to the carrier, especially in cases which require the presence and retention of the liquid (aqueous) phase to facilitate completion of covalent bonding in the system substance-carrier.

Figure 4A:
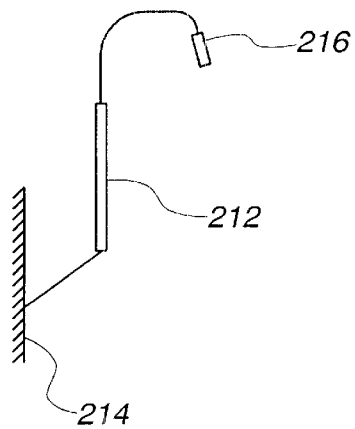
FIGS. 4A–B is a schematic view of an intercalating compound revealing a duplexed pair of oligonucleotide molecules juxtaposed to a polyacrylamide matrix, in accordance with the present invention.
Figure 4B:
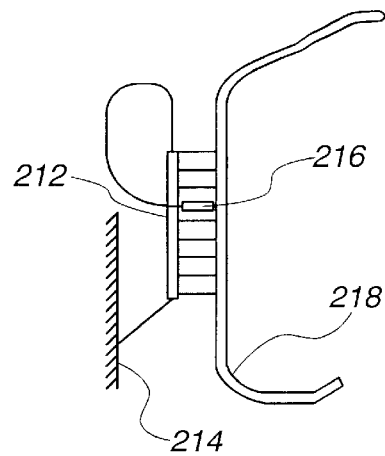

An exemplary embodiment of the duplex detection method, incorporating the produced micro-matrix topologies, is schematically depicted in FIGS. 4A–B as numeral 200. FIG. 4A depicts an oligomer, 212, immobilized to a gel matrix unit 214. The oligomer is constructed to contain an intercalating tag, 216 such as ethidium bromide. Other intercalating agents, such as propidium iodide, also can be employed.

In the free state, depicted in FIG. 4A, wherein the intercalating agent is not juxtaposed between base planes of a duplex, the tag fluoresces at a certain intensity. Part of this fluorescence is due to higher background and lower-signal-to-background noise that results from intercalating dyes reacting with single-stranded oligonucleotides. However, fluorescence is magnified far above background levels when duplexes do occur. As can be noted in FIG. 4B, when a single strand 218 of a target oligonucleotide molecule, complementary to the immobilized oligomer, is contacted with the loaded gel unit, duplexing occurs. The inventors observed that the intercalating agent, now juxtaposed between the base planes of the duplex, fluoresces at an intensity that is approximately 10 times that observed in the free state. This higher intensity is observed within approximately one minute.

As an alternative to first binding the intercalating agent to the immobilized oligomer, the intercalating agent can instead be bound to the target single strand oligonucleotide molecule 218. In yet another alternative, addition of the intercalating agent can be made after duplexing occurs between the immobilized oligo fraction 212 and the mobilized single strand target sequence 218.

For example, fluorescence enhancements are achieved when intercalating dyes such as thiazole orange homodimer (TOTO) or oxazole yellow homodimer (YOYO), both of which are manufactured by Molecular Probes, Eugene Oregon. DNA binding fluorochromes specific for double-stranded DNA also provide good results.

Use of AT-specific fluorescent ligands that stabilize these pairs also enhance the fluorescent process by equalizing AT stability vis-a-vis GC-rich interactions.

EXAMPLE

Figure 5A:
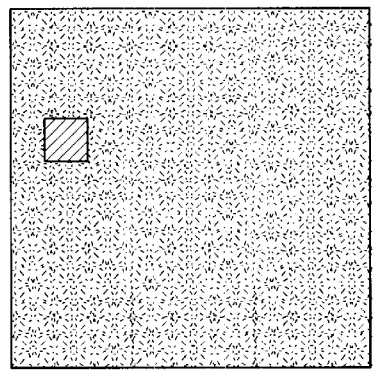
FIGS. 5A–B is a plan view of a gel matrix disclosing the existence of duplexes when fluorescently labeled oligomer (I) is used, and when intercalating dye (II) is used to detect duplexes, in accordance with the present invention.
Figure 5B:
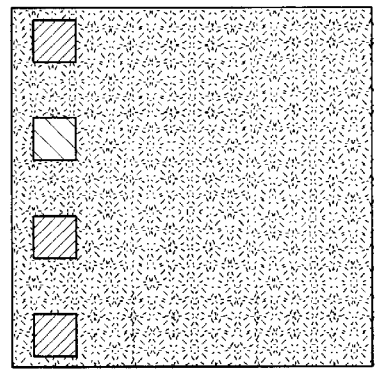
Figure 6:
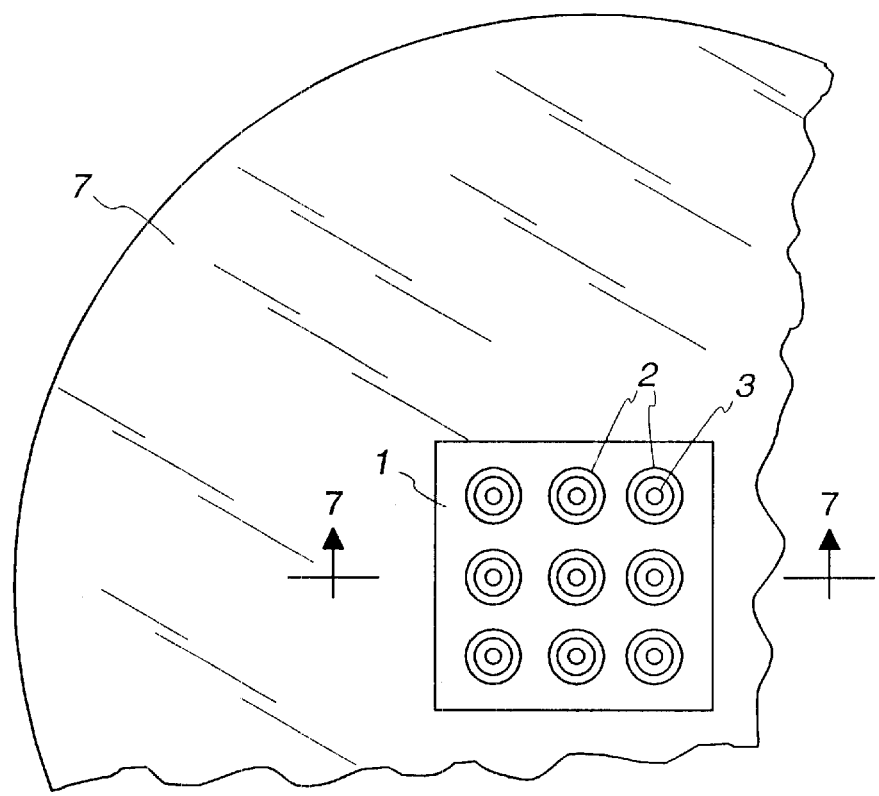
FIG. 6. is a plan view of a device for micro dispensing aqueous solutions, in accordance with features of the invention.
Figure 7:
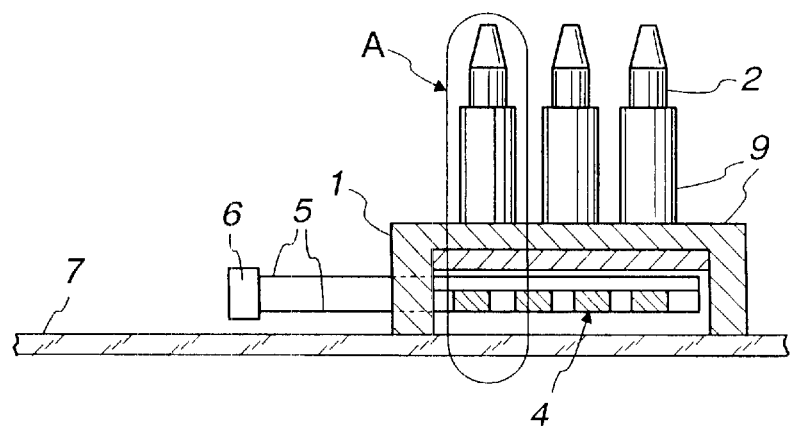
FIG. 7 is an elevational, cross-sectional view of FIG. 6, taken along line 7—7.
Figure 8:
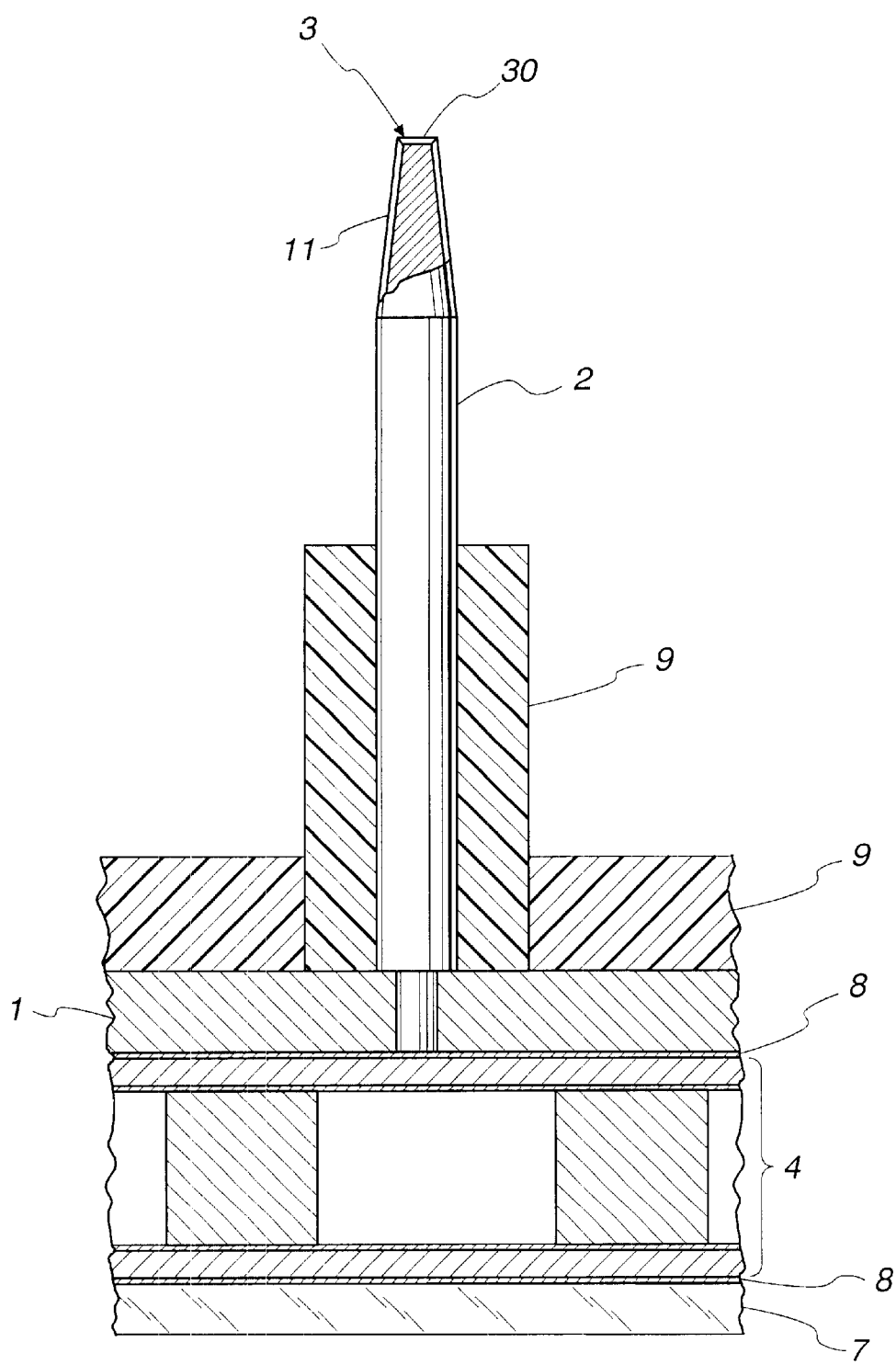
FIG. 8 is an elevational, cross-sectional view of one of the micro dispensing probes, in accordance with features of the invention.
Figure 9:
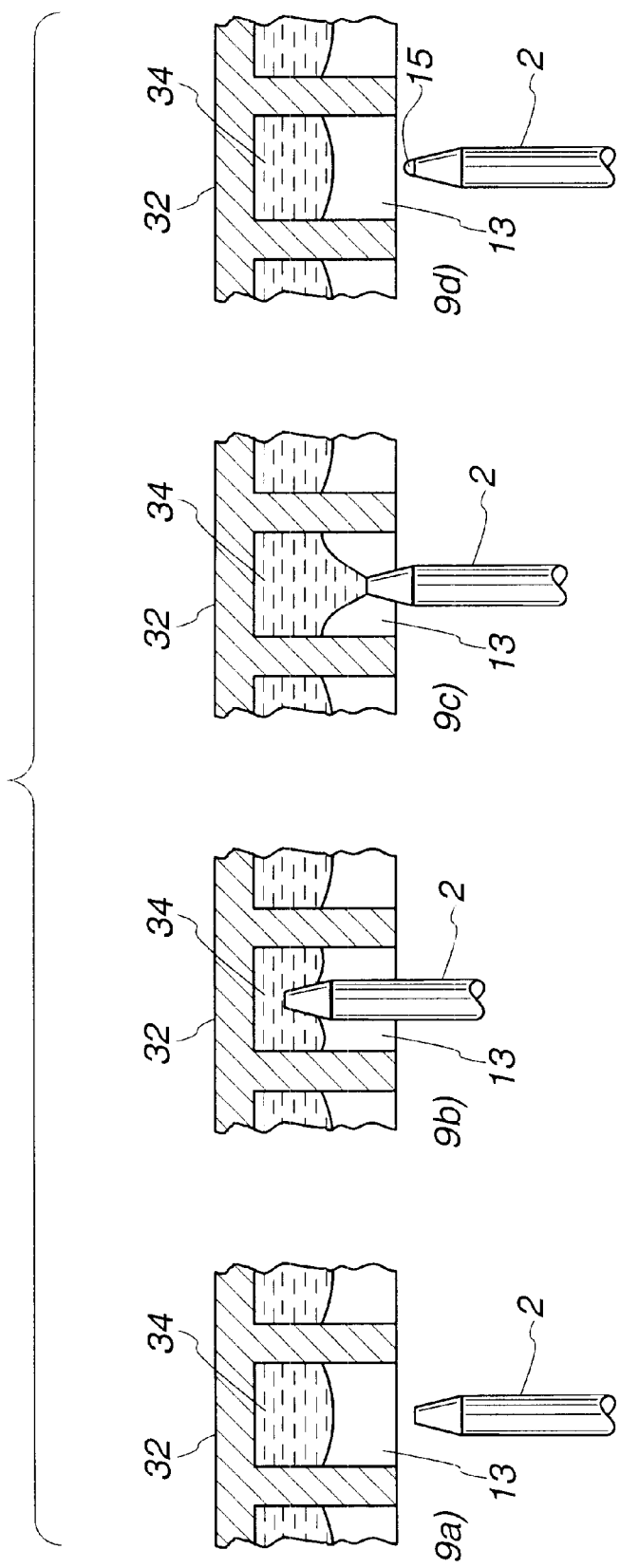
FIGS. 9A–9D is a detailed view of harvesting of aqueous solutions, in accordance with features of the invention.
Figure 10:
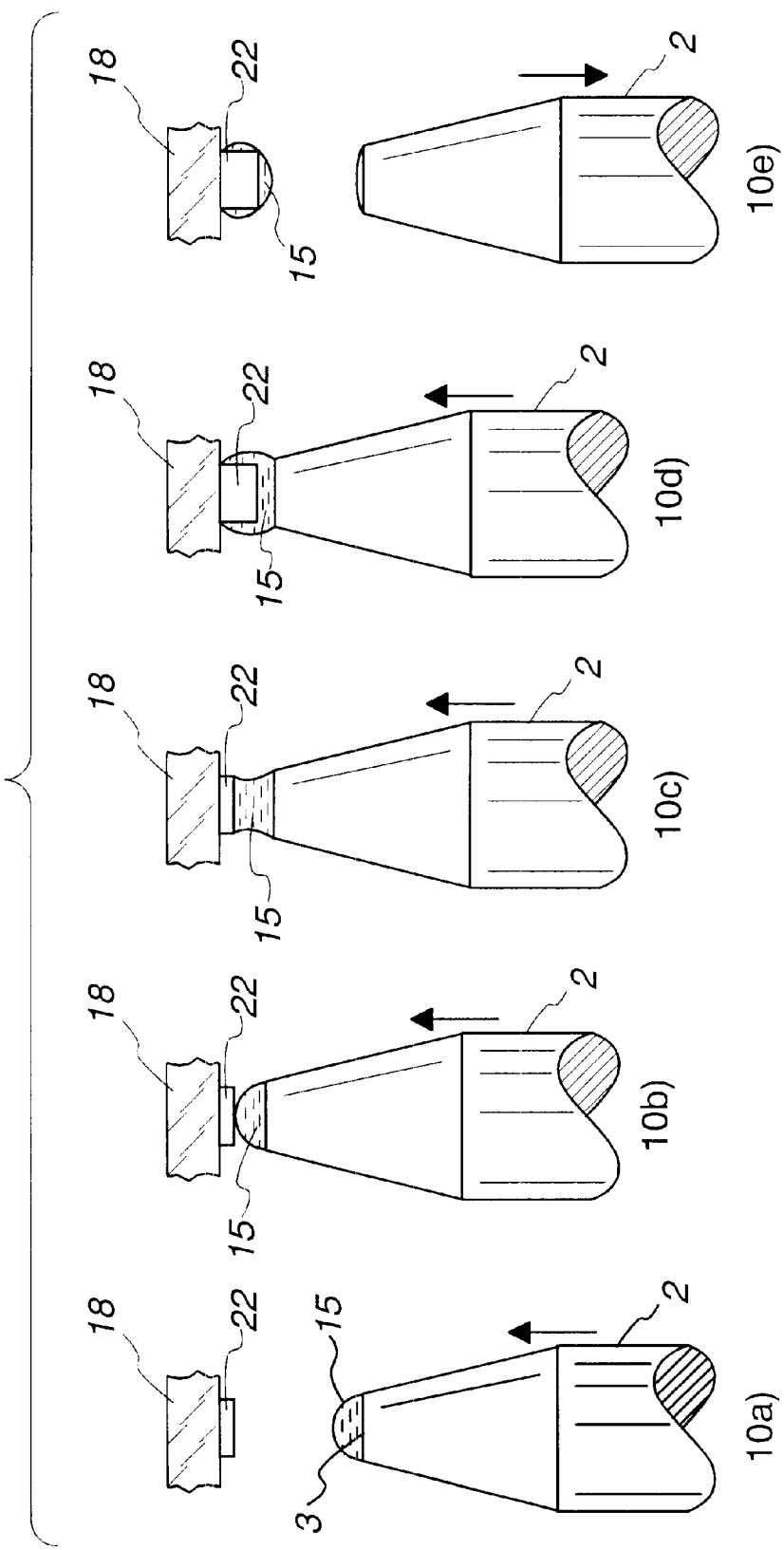
FIGS. 10A–10E is a detailed view of the deposition of aqueous solutions, in accordance with features of the invention.

FIG. 5 illustrates the efficiency of using either fluorescently labeled target ss DNA strings (I) or intercalating dyes (II) to rapidly detect duplex formation. This plan view depicts the same matrix of polyacrylamide cells, whereby the matrix is manufactured by the methods disclosed supra. The matrix is comprised of 16 cells, each cell loaded with the octamer CyAACCxT-5'. As shown, the 3' end is anchored to the gel and not available for further interaction. The immobilized octamer varies at two base positions "y" and "x" as shown along the boundaries of the matrix.

As can be determined in FIG. 5 (I), when the octamer-loaded matrix is hybridized with fluorescently labeled ss DNA, such as the 19-mer CCTGGGCAGGTTGGTATCA, a clear signal is seen when a perfect GC and TA match is made at duplexing. The fluorescent label used in this instance was HEX, available through Applied Biosystems, Foster City, Calif. Another suitable dye is tetramethylrodamine.

In a separate experiment, when the octamer-loaded matrix is hybridized with the unlabeled 19-mer in the presence of an intercalating agent, a clear signal again is seen at the GC and TA matching cell location. This can be noted in FIG. 4 (II). Weaker signals also are detected, however. For example, signals were observed when just TA or GC interaction was observed. This indicates that when background noise is controlled, the use of an intercalating agent or a plurality of intercalating agents may be more sensitive, than the use of fluorescent dyes, for detecting at least partial matches when rapid determinations are desired. The intercalating agent used in this instance, ethidium bromide, was added after the duplexing between oligomer strings occurred.

However, and as discussed supra, intercalating agents also can be first attached to either the shorter oligomer strand prior to immobilization. Alternatively, the intercalating agent could be attached to the target single strand prior to hybridization.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for constructing oligonucleotide matrices comprising:
   a) confining light sensitive fluid to a surface;
   b) exposing said light-sensitive fluid to a light pattern so as to cause the fluid exposed to the light to coalesce into discrete units and stick to the surface;
   c) contacting each of the units with a set of different oligonucleotide molecules so as to allow the molecules to disperse into the units, wherein the light sensitive fluid is comprised of methylene blue solution, acrylamide solution and TEMED.

2. The method as recited in claim 1 wherein the light pattern consists of a series of squares.

3. The method as recited in claim 2 wherein the squares have dimensions ranging from between 25 microns by 25 microns to 1,000 microns by 1,000 microns.

4. The method as recited in claim 1 wherein the steps of exposing said light-sensitive fluid to a light pattern so as to cause the fluid exposed to the light to coalesce into discrete units and stick to the surface further comprises:
   a) supplying a transparent substrate with a first side and a second side;
   b) applying an opaque photomask to said first side of the substrate;
   c.) removing predetermined portions of the photomask to effect a predetermined pattern;
   d) contacting said first side of said substrate to a light sensitive fluid;
   e) exposing said second side of said substrate to light so as to cause the fluid juxtaposed to said pattern to coalesce; and
   f) removing said light.

5. The method as recited in claim 1 wherein the wavelength of light is in the ultra-violet range.

6. The method as recited in claim 5 wherein the ultra violet light has a wavelength of 312 nanometers.

7. A method for constructing oligonucleotide matrices comprising:
   a) confining light sensitive fluid to a surface;
   b) exposing said light-sensitive fluid to a light pattern so as to cause the fluid exposed to the light to coalesce into discrete units and stick to the surface; and
   c) contacting each of the units with a set of different oligonucleotide molecules so as to allow the molecules to disperse into the units, wherein the light sensitive fluid is comprised of a radical producing agent, acrylamide solution and TEMED.

8. The method as recited in claim 1 wherein light is utilized having a wavelength of between approximately 180 nm and 650 nm.

9. The method as recited in claim 1 wherein the light sensitive fluid is exposed in an oxygen depleted environment.

10. The method as recited in claim 1 wherein the light pattern contains a means for regulating the concentration of the light sensitive fluid.

11. A method for constructing oligonucleotide matrices comprising:
   a) confining light sensitive monomer solution to a surface, wherein said solution contains an acrylamide;
   b) exposing said light sensitive monomer to a light pattern so as to cause the monomer solution exposed to the light to polymerize into discrete gel units and stick to the surface; and
   c) contacting each of the unit with a set of different oligonucleotide molecules so as to allow the molecules to disperse into the units and covalently link to molecules comprising the gel units.

12. The method as recited in claim 11 wherein the light sensitive monomer is a radical producing agent.

13. The method as recited in claim 11 wherein the agent produces radicals when subjected to UV radiation.

14. The method as recited in claim 12 wherein the radical producing agent is a compound selected from the group consisting of, 2,2-dimethoxy-2-phenyl acetophenone; dimethylamino-pyridine; 3,5-diiodo-4pyridone-1-acetic acid; 4,4'azobis(4-cyanovaleric acid); 4(dimethylamino) phenethyl alcohol; and acetone.

15. The method as recited in claim 11 wherein the step of contacting each of the units with a set of different oligonucleotide molecules further comprises:
   d) contacting the gel pads with a mixture of chloroform and reducing agent so as to form a layer of the mixture over the gel pads;
   e) contacting the layer with water in an amount sufficient to cause the gel pads to swell in the presence of the water and for a sufficient time so as to cause covalent linking to occur between the oligonucleotides and constituents of each the gel units.

16. The method as recited in claim 11 wherein the pattern is composed of individual geometrically distinct units.

17. The method as recited in claim 16 wherein the geometrically distinct units are three-dimensional shapes.

18. The method as recited in claim 11 wherein the polymerization occurs in an oxygen depleted atmosphere.

19. The method as recited in claim 17 wherein the three-dimensional shapes are cubes, rods, pyramids, polygons, intersecting parallel bipeds, and combinations thereof.

20. The method as recited in 11, wherein the light pattern contains a means for regulating the concentration of the light sensitive fluid.

* * * * *